(12) United States Patent  
Diolaiti et al.

(10) Patent No.: US 11,992,188 B2
(45) Date of Patent: *May 28, 2024

(54) SYSTEMS AND METHODS FOR DETECTING ENVIRONMENTAL FORCES ON AN ELONGATE DEVICE

(71) Applicant: INTUITIVE SURGICAL OPERATIONS, INC., Sunnyvale, CA (US)

(72) Inventors: Nicola Diolaiti, Menlo Park, CA (US); Federico Barbagli, San Francisco, CA (US); Samuel Y. Chang, Mountain View, CA (US); Vincent Duindam, San Francisco, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/308,906

(22) Filed: Apr. 28, 2023

(65) Prior Publication Data

US 2023/0263373 A1    Aug. 24, 2023

Related U.S. Application Data

(63) Continuation of application No. 16/754,939, filed as application No. PCT/US2018/054571 on Oct. 5, 2018, now Pat. No. 11,672,412.

(Continued)

(51) Int. Cl.
*A61B 1/005* (2006.01)
*A61B 17/00* (2006.01)
(Continued)

(52) U.S. Cl.
CPC ............ *A61B 1/0051* (2013.01); *A61B 1/005* (2013.01); *A61B 1/009* (2022.02);
(Continued)

(58) Field of Classification Search
CPC ....... A61B 1/005; A61B 1/0051; A61B 1/009; A61B 1/2676; A61B 17/00234;
(Continued)

(56) References Cited

U.S. PATENT DOCUMENTS 11,672,412 B2 *  6/2023  Diolaiti .................. A61B 1/009
                                                606/108
2005/0119527 A1  6/2005  Banik et al.
(Continued)

FOREIGN PATENT DOCUMENTS

WO    WO-2016191298 A1   12/2016

OTHER PUBLICATIONS

International Preliminary Report on Patentability for Application No. PCT/US2018/054571, dated Apr. 23, 2020, 17 pages.
(Continued)

*Primary Examiner* — Michael T Rozanski
(74) *Attorney, Agent, or Firm* — Haynes & Boone, LLP

(57) ABSTRACT

A medical system includes a flexible elongate instrument and a control unit. The control unit is configured to determine a force exerted by the flexible elongate instrument on tissue of a patient, determine a driving state of the flexible elongate instrument, set a force threshold based on the driving state, and provide feedback to an operator in response to the determined force being higher than the force threshold. Different driving states are associated with different force thresholds.

20 Claims, 5 Drawing Sheets

Related U.S. Application Data

(60) Provisional application No. 62/572,257, filed on Oct. 13, 2017.

(51) Int. Cl.
*A61B 34/00* (2016.01)
*A61B 34/20* (2016.01)
*A61B 34/30* (2016.01)
*A61B 90/00* (2016.01)

(52) U.S. Cl.
CPC ........ *A61B 17/00234* (2013.01); *A61B 34/20* (2016.02); *A61B 34/76* (2016.02); *A61B 2017/0011* (2013.01); *A61B 2017/00115* (2013.01); *A61B 2017/00296* (2013.01); *A61B 2034/2048* (2016.02); *A61B 2034/2061* (2016.02); *A61B 2034/301* (2016.02); *A61B 2090/065* (2016.02); *A61B 2562/0261* (2013.01)

(58) Field of Classification Search
CPC .. A61B 2017/0011; A61B 2017/00115; A61B 2017/00296; A61B 2034/2048; A61B 2034/2061; A61B 2034/304; A61B 2090/065; A61B 2562/0261; A61B 34/20; A61B 34/76

See application file for complete search history.

(56) References Cited

U.S. PATENT DOCUMENTS

| | | |
|---|---|---|
| 2007/0197939 A1 | 8/2007 | Wallace et al. |
| 2013/0204124 A1 | 8/2013 | Duindam et al. |
| 2016/0157939 A1 | 6/2016 | Larkin et al. |
| 2020/0253669 A1 | 8/2020 | Diolaiti et al. |

OTHER PUBLICATIONS

International Search Report and Written Opinion for Application No. PCT/US2018/054571, dated Jan. 30, 2019, 21 pages (ISRG10770/PCT).

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

SYSTEMS AND METHODS FOR DETECTING ENVIRONMENTAL FORCES ON AN ELONGATE DEVICE

CROSS-REFERENCE TO RELATED APPLICATIONS

This application is a continuation of U.S. patent application Ser. No. 16/754,939, filed Apr. 9, 2020, which is the U.S. national phase of International Application No. PCT/US2018/054571, filed Oct. 5, 2018, which designated the U.S. and claims the priority to and benefit of U.S. Provisional Patent Application No. 62/572,257, filed Oct. 13, 2017, entitled "Systems and Methods for Detecting Unsafe Environmental Forces on an Elongate Device," all of which are incorporated by reference herein in their entirety.

FIELD

The present disclosure is directed to systems and methods for detecting environmental forces on an elongate device.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions clinicians may insert minimally invasive medical instruments (including surgical, diagnostic, therapeutic, or biopsy instruments) to reach a target tissue location. One such minimally invasive technique is to use a flexible and/or steerable elongate device, such as a catheter, that can be inserted into anatomic passageways and navigated toward a region of interest within the patient anatomy. Control of such an elongate device by medical personnel involves the management of several degrees of freedom including at least the management of insertion and retraction of the elongate device as well as steering of the device. In addition, different modes of operation may also be supported.

Operation of a medical device, such as a flexible and/or steerable elongate device within the body of a patient presents risks to the patient because the flexible and/or steerable elongate device may cause undesired damage to the patient's tissue if the flexible and/or steerable elongate device is operated with excessive force. When the elongate device is directly controlled by an operator, such as a surgeon, force exerted by the elongate device on the anatomy of the patient and conversely the force exerted on the elongate device by the tissue of the patient may often be felt directly by the operator and can be limited by the operator by exerting greater or lesser force on the proximal end of the elongate device. However, when the elongate device is controlled teleoperatively, the operator is not able to directly sense the forces being exerted and this increases the risks that an excessive force may be exerted and the places the patient and/or the elongate device in unacceptable danger.

Accordingly, it would be advantageous to provide systems and methods that help determine the forces being exerted on an elongate device, assessing whether those forces are excessive, and providing appropriate feedback to an operator to reduce the risks of excessive forces being exerted.

SUMMARY

The embodiments of the invention are best summarized by the claims that follow the description.

Consistent with some embodiments, a medical device includes a flexible elongate instrument, an actuator for inserting and retracting the flexible elongate instrument, and a control unit. The control unit is configured to determine a force exerted by the flexible elongate instrument on tissue of a patient. The force is determined based on one or more of a shape of the flexible elongate instrument, a force being exerted by the actuator, or an amount of force being applied at a proximal end of the flexible elongate instrument.

Consistent with some embodiments, a medical system includes a flexible elongate instrument, and a control unit. The control unit is configured to determine a force exerted by the flexible elongate instrument on tissue of a patient, determine a driving state of the flexible elongate instrument, set a force threshold based on the driving state, and provide feedback to an operator in response to the determined force being higher than the force threshold.

Consistent with some embodiments, a method of operating a medical device includes determining a shape of a flexible elongate instrument, determining one or more of a first force being exerted by an actuator used to drive the flexible elongate instrument, a second force being applied to a proximal end of the flexible elongate instrument, or a third force exerted by the flexible elongate instrument on tissue of a patient based on the shape, the first force, and the second force.

Consistent with some embodiments, a method of operating a medical system includes determining a force exerted by a flexible elongate instrument on tissue of a patient, determining a driving state of the flexible elongate instrument, setting a force threshold based on the driving state, and providing feedback to an operator in response to the determined force being higher than the force threshold.

Consistent with some embodiments, a non-transitory machine-readable medium includes a plurality of machine-readable instructions which when executed by one or more processors associated with a device are adapted to cause the one or more processors to perform a method. The method includes determining one or more of a shape of a flexible elongate instrument, a first force being exerted by an actuator used to drive the flexible elongate instrument, or a second force being applied to a proximal end of the flexible elongate instrument, and determining a third force exerted by the flexible elongate instrument on tissue of a patient based on the shape, the first force, and the second force.

Consistent with some embodiments, a non-transitory machine-readable medium includes a plurality of machine-readable instructions which when executed by one or more processors associated with a device are adapted to cause the one or more processors to perform a method. The method includes determining a force exerted by a flexible elongate instrument on tissue of a patient, determining a driving state of the flexible elongate instrument, setting a force threshold based on the driving state, and providing feedback to an operator in response to the determined force being higher than the force threshold.

Consistent with some embodiments, a non-transitory machine-readable medium includes a plurality of machine-readable instructions which when executed by one or more processors associated with a device are adapted to cause the one or more processors to perform a method. The method includes determining a first force exerted by a flexible elongate instrument on tissue of a patient, determining a driving state of the flexible elongate instrument, setting a force threshold based on the driving state, and providing feedback to an operator in response to the determined first force being higher than the force threshold.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Figure 1:
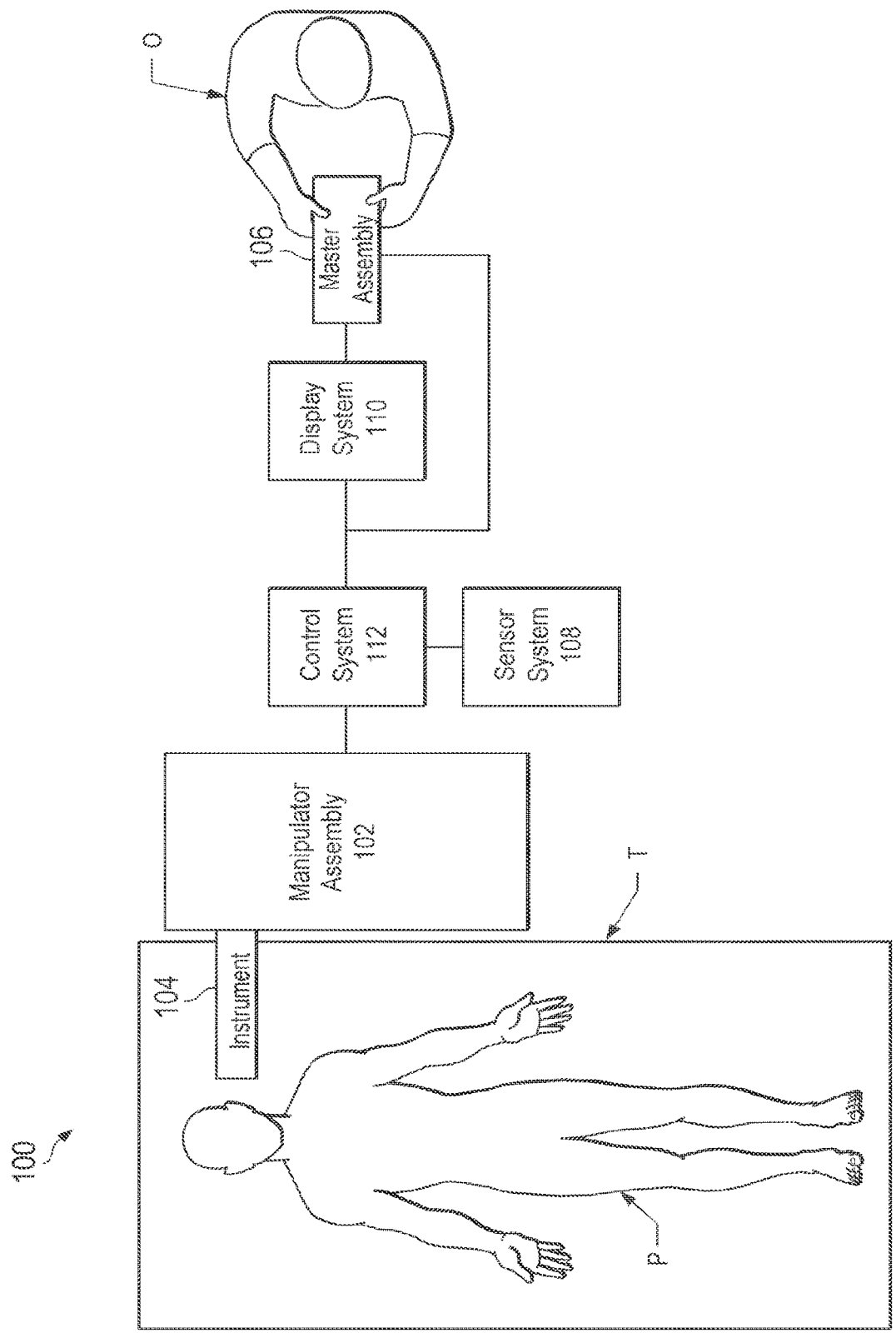
FIG. 1 is a simplified diagram of a teleoperated medical system according to some embodiments.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

Any reference to surgical instruments and surgical methods is non-limiting as the instruments and methods described herein may be used for animals, human cadavers, animal cadavers, portions of human or animal anatomy, non-surgical diagnosis, industrial systems, and general robotic or teleoperational systems.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

FIG. 1 is a simplified diagram of a teleoperated medical system 100 according to some embodiments. In some embodiments, teleoperated medical system 100 may be suitable for use in, for example, surgical, diagnostic, therapeutic, or biopsy procedures. As shown in FIG. 1, medical system 100 generally includes a teleoperational manipulator assembly 102 for operating a medical instrument 104 in performing various procedures on a patient P. Teleoperational manipulator assembly 102 is mounted to or near an operating table T. A master assembly 106 allows an operator O (e.g., a surgeon, a clinician, or a physician as illustrated in FIG. 1) to view the interventional site and to control teleoperational manipulator assembly 102.

Master assembly 106 may be located at an operator's console which is usually located in the same room as operating table T, such as at the side of a surgical table on which patient P is located. However, it should be understood that operator O can be located in a different room or a completely different building from patient P. Master assembly 106 generally includes one or more control devices for controlling teleoperational manipulator assembly 102. The control devices may include any number of a variety of input devices, such as joysticks, trackballs, data gloves, trigger-guns, hand-operated controllers, voice recognition devices, body motion or presence sensors, and/or the like. To provide operator O a strong sense of directly controlling instruments 104 the control devices may be provided with the same degrees of freedom as the associated medical instrument 104. In this manner, the control devices provide operator O with telepresence or the perception that the control devices are integral with medical instruments 104.

In some embodiments, the control devices may have more or fewer degrees of freedom than the associated medical instrument 104 and still provide operator O with telepresence. In some embodiments, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

Teleoperational manipulator assembly 102 supports medical instrument 104 and may include a kinematic structure of one or more non-servo controlled links (e.g., one or more links that may be manually positioned and locked in place, generally referred to as a set-up structure) and a teleoperational manipulator. Teleoperational manipulator assembly 102 may optionally include a plurality of actuators or motors that drive inputs on medical instrument 104 in response to commands from the control system (e.g., a control system 112). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to medical system 100 describing the rotation and orientation of the motor shafts. This position sensor data may be used to determine motion of the objects manipulated by the actuators.

Teleoperated medical system 100 may include a sensor system 108 with one or more sub-systems for receiving information about the instruments of teleoperational manipulator assembly 102. Such sub-systems may include a position/location sensor system (e.g., an electromagnetic (EM) sensor system); a shape sensor system for determining the position, orientation, speed, velocity, pose, and/or shape of a distal end and/or of one or more segments along a flexible body that may make up medical instrument 104; and/or a visualization system for capturing images from the distal end of medical instrument 104.

Teleoperated medical system 100 also includes a display system 110 for displaying an image or representation of the surgical site and medical instrument 104 generated by subsystems of sensor system 108. Display system 110 and master assembly 106 may be oriented so operator O can control medical instrument 104 and master assembly 106 with the perception of telepresence.

In some embodiments, medical instrument 104 may have a visualization system (discussed in more detail below), which may include a viewing scope assembly that records a concurrent or real-time image of a surgical site and provides the image to the operator or operator O through one or more displays of medical system 100, such as one or more displays of display system 110. The concurrent image may be, for example, a two or three dimensional image captured by an endoscope positioned within the surgical site. In some embodiments, the visualization system includes endoscopic components that may be integrally or removably coupled to medical instrument 104. However in some embodiments, a separate endoscope, attached to a separate manipulator assembly may be used with medical instrument 104 to image the surgical site. In some examples, the endoscope may include one or more mechanisms for cleaning one or more lenses of the endoscope when the one or more lenses become partially and/or fully obscured by fluids and/or other materials encountered by the endoscope. In some examples, the one or more cleaning mechanisms may optionally include an air and/or other gas delivery system that is usable to emit a puff of air and/or other gasses to blow the one or more lenses clean. Examples of the one or more cleaning mechanisms are discussed in more detail in International Publication No. WO/2016/025465 (filed Aug. 11, 2016) (disclosing "Systems and Methods for Cleaning an Endoscopic Instrument"), which is incorporated by reference herein in its entirety. The visualization system may be implemented as hardware, firmware, software or a combination thereof which interact with or are otherwise executed by one or more computer processors, which may include the processors of a control system 112.

Display system 110 may also display an image of the surgical site and medical instruments captured by the visualization system. In some examples, teleoperated medical system 100 may configure medical instrument 104 and controls of master assembly 106 such that the relative positions of the medical instruments are similar to the relative positions of the eyes and hands of operator O. In this manner operator O can manipulate medical instrument 104 and the hand control as if viewing the workspace in substantially true presence. By true presence, it is meant that the presentation of an image is a true perspective image simulating the viewpoint of an operator that is physically manipulating medical instrument 104.

In some examples, display system 110 may present images of a surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including e.g., time based or velocity based information) images and/or as images from models created from the pre-operative or intra-operative image data sets.

In some embodiments, often for purposes of imaged guided surgical procedures, display system 110 may display a virtual navigational image in which the actual location of medical instrument 104 is registered (i.e., dynamically referenced) with the preoperative or concurrent images/model. This may be done to present the operator O with a virtual image of the internal surgical site from a viewpoint of medical instrument 104. In some examples, the viewpoint may be from a tip of medical instrument 104. An image of the tip of medical instrument 104 and/or other graphical or alphanumeric indicators may be superimposed on the virtual image to assist operator O controlling medical instrument 104. In some examples, medical instrument 104 may not be visible in the virtual image.

In some embodiments, display system 110 may display a virtual navigational image in which the actual location of medical instrument 104 is registered with preoperative or concurrent images to present the operator O with a virtual image of medical instrument 104 within the surgical site from an external viewpoint. An image of a portion of medical instrument 104 or other graphical or alphanumeric indicators may be superimposed on the virtual image to assist operator O in the control of medical instrument 104. As described herein, visual representations of data points may be rendered to display system 110. For example, measured data points, moved data points, registered data points, and other data points described herein may be displayed on display system 110 in a visual representation. The data points may be visually represented in a user interface by a plurality of points or dots on display system 110 or as a rendered model, such as a mesh or wire model created based on the set of data points. In some examples, the data points may be color coded according to the data they represent. In some embodiments, a visual representation may be refreshed in display system 110 after each processing operation has been implemented to alter data points.

Teleoperated medical system 100 may also include control system 112. Control system 112 includes at least one memory and at least one computer processor (not shown) for effecting control between medical instrument 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the system may include two or more data processing circuits with one portion of the processing optionally being performed on or adjacent to teleoperational manipulator assembly 102, another portion of the processing being performed at master assembly 106, and/or the like. The processors of control system 112 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may receive force and/or torque feedback from medical instrument 104. Responsive to the feedback, control system 112 may transmit signals to master assembly 106. In some examples, control system 112 may transmit signals instructing one or more actuators of teleoperational manipulator assembly 102 to move medical instrument 104. Medical instrument 104 may extend into an internal surgical site within the body of patient P via openings in the body of patient P. Any suitable conventional and/or specialized actuators may be used. In some examples, the one or more actuators may be separate from, or integrated with, teleoperational manipulator assembly 102. In some embodiments, the one or more actuators and teleoperational manipulator assembly 102 are provided as part of a teleoperational cart positioned adjacent to patient P and operating table T.

Control system 112 may optionally further include a virtual visualization system to provide navigation assistance to operator O when controlling medical instrument 104 during an image-guided surgical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. Software, which may be used in combination with manual inputs, is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively during a clinical procedure. In some embodiments, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, sensor system 108 may be used to compute an approximate location of medical instrument 104 with respect to the anatomy of patient P. The location can be used to produce both macro-level (external) tracking images of the anatomy of patient P and virtual internal images of the anatomy of patient P. The system may implement one or more electromagnetic (EM) sensor, fiber optic sensors, and/or other sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety, discloses one such system. Teleoperated medical system 100 may further include optional operations and support systems (not shown) such as illumination systems, steering control systems, irrigation systems, and/or suction systems. In some embodiments, teleoperated medical system 100 may include more than one teleoperational manipulator assembly and/or more than one master assembly. The exact number of teleoperational manipulator assemblies will depend on the surgical procedure and the space constraints within the operating room, among other factors. Master assembly 106 may be collocated or they may be positioned in separate locations. Multiple master assemblies allow more than one operator to control one or more teleoperational manipulator assemblies in various combinations.

Figure 2A:
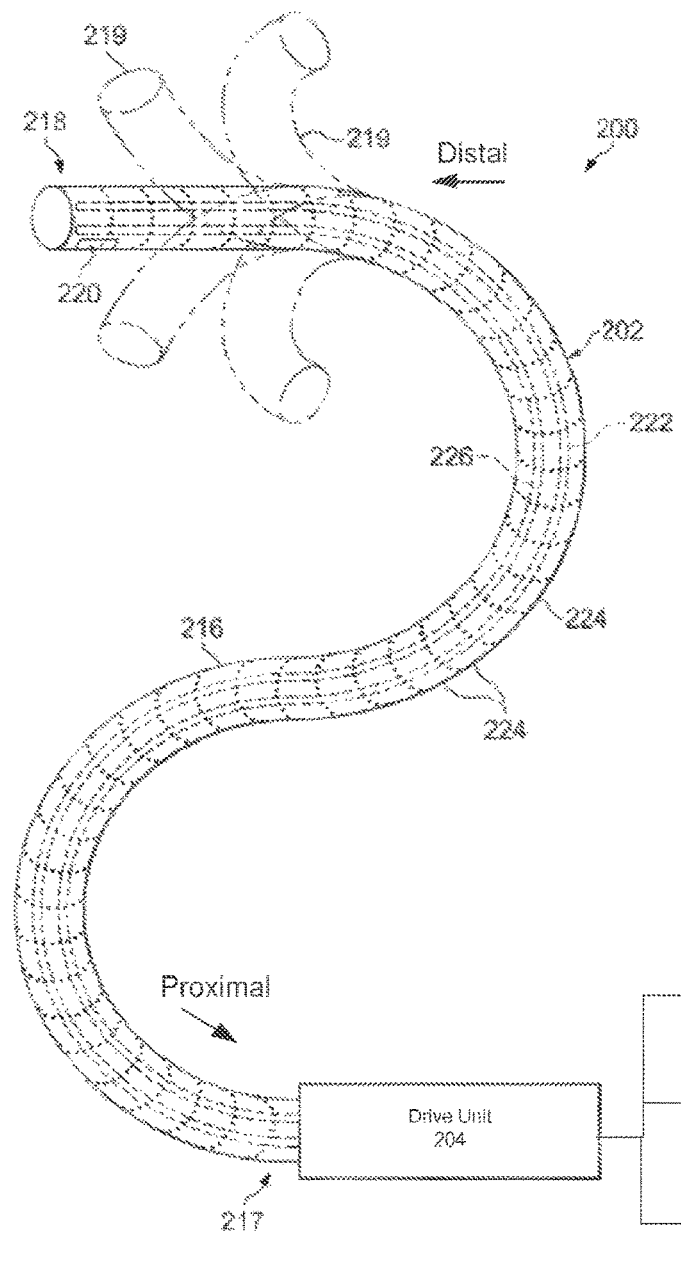
FIG. 2A is a simplified diagram of a medical instrument system according to some embodiments.

FIG. 2A is a simplified diagram of a medical instrument system 200 according to some embodiments. In some embodiments, medical instrument system 200 may be used as medical instrument 104 in an image-guided medical procedure performed with teleoperated medical system 100. In some examples, medical instrument system 200 may be used for non-teleoperational exploratory procedures or in procedures involving traditional manually operated medical instruments, such as endoscopy. Optionally medical instrument system 200 may be used to gather (i.e., measure) a set of data points corresponding to locations within anatomic passageways of a patient, such as patient P.

Medical instrument system 200 includes elongate device 202, such as a flexible catheter, coupled to a drive unit 204. Elongate device 202 includes a flexible body 216 having proximal end 217 and distal end or tip portion 218. In some embodiments, flexible body 216 has an approximately 3 mm outer diameter. Other flexible body outer diameters may be larger or smaller.

Medical instrument system 200 further includes a tracking system 230 for determining the position, orientation, speed, velocity, pose, and/or shape of distal end 218 and/or of one or more segments 224 along flexible body 216 using one or more sensors and/or imaging devices as described in further detail below. In some examples, flexible body 216 may include one or more fiducial markers that may tracked by tracking system 230 to determine the position, orientation, speed, velocity, pose, and/or shape of distal end 218 and/or of the one or more segments 224 along flexible body 216. The entire length of flexible body 216, between distal end 218 and proximal end 217, may be effectively divided into segments 224. If medical instrument system 200 is consistent with medical instrument 104 of a teleoperated medical system 100, tracking system 230. Tracking system 230 may optionally be implemented as hardware, firmware, software or a combination thereof which interact with or are otherwise executed by one or more computer processors, which may include the processors of control system 112 in FIG. 1.

Tracking system 230 may optionally track distal end 218 and/or one or more of the segments 224 using a shape sensor 222. Shape sensor 222 may optionally include an optical fiber aligned with flexible body 216 (e.g., provided within an interior channel (not shown) or mounted externally). In one embodiment, the optical fiber has a diameter of approximately 200 μm. In other embodiments, the dimensions may be larger or smaller. The optical fiber of shape sensor 222 forms a fiber optic bend sensor for determining the shape of flexible body 216. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. Pat. No. 7,781,724 (disclosing "Fiber Optic Position and Shape Sensing Device and Method Relating Thereto"); U.S. Pat. No. 7,772,541 (disclosing "Fiber Optic Position and/or Shape Sensing Based on Rayleigh Scatter"); and U.S. Pat. No. 6,389,187 (disclosing "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. In some embodiments, the shape of the elongate device may be determined using other techniques. For example, a history of the distal end pose of flexible body 216 can be used to reconstruct the shape of flexible body 216 over the interval of time. In some embodiments, tracking system 230 may optionally and/or additionally track distal end 218 using a position sensor system 220. Position sensor system 220 may comprise, or be a component of an EM sensor system including one or more conductive coils that may be subjected to an externally generated electromagnetic field. Each coil of such an EM sensor system used to implement position sensor system 220 then produces an induced electrical signal having characteristics that depend on the position and orientation of the coil relative to the externally generated electromagnetic field. In some embodiments, position sensor system 220 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

In some embodiments, tracking system 230 may alternately and/or additionally rely on historical pose, position, or orientation data stored for a known point of an instrument system along a cycle of alternating motion, such as breathing. This stored data may be used to develop shape information about flexible body 216. In some examples, a series of positional sensors (not shown), such as electromagnetic (EM) sensors similar to the sensors in embodiments of position sensor system 220 may be positioned along flexible body 216 and then used for shape sensing. In some examples, a history of data from one or more of these sensors taken during a procedure may be used to represent the shape of elongate device 202, particularly if an anatomic passageway is generally static.

Figure 2B:
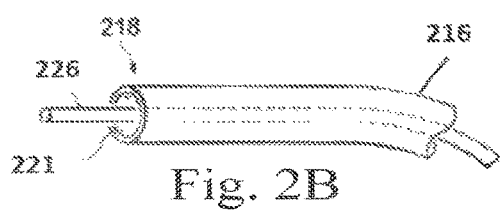
FIG. 2B is a simplified diagram of a medical instrument with an extended medical tool according to some embodiments.

Flexible body 216 includes a channel 221 sized and shaped to receive a medical instrument 226. FIG. 2B is a simplified diagram of flexible body 216 with medical instrument 226 extended according to some embodiments. In some embodiments, medical instrument 226 may be used for procedures such as surgery, biopsy, ablation, illumination, irrigation, or suction. Medical instrument 226 can be deployed through channel 221 of flexible body 216 and used at a target location within the anatomy. Medical instrument 226 may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. In various embodiments, medical instrument 226 is a biopsy instrument, which may be used to remove sample tissue or a sampling of cells from a target anatomic location. Medical instrument 226 may be used with an image capture probe also within flexible body 216. In various embodiments, medical instrument 226 may be an image capture probe that includes a distal portion with a stereoscopic or monoscopic camera at or near distal end 218 of flexible body 216 for capturing images (including video images) that are processed by a visualization system 231 for display and/or provided to tracking system 230 to support tracking of distal end 218 and/or one or more of the segments 224. The image capture probe may include a cable coupled to the camera for transmitting the captured image data. In some examples, the image capture instrument may be a fiber-optic bundle, such as a fiberscope, that couples to visualization system 231. The image capture instrument may be single or multi-spectral, for example capturing image data in one or more of the visible, infrared, and/or ultraviolet spectrums. Alternatively, medical instrument 226 may itself be the image capture probe. Medical instrument 226 may be advanced from the opening of channel 221 to perform the procedure and then retracted back into the channel when the procedure is complete. Medical instrument 226 may be removed from proximal end 217 of flexible body 216 or from another optional instrument port (not shown) along flexible body 216.

Medical instrument 226 may additionally house cables, linkages, or other actuation controls (not shown) that extend between its proximal and distal ends to controllably the bend distal end of medical instrument 226. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

Flexible body 216 may also house cables, linkages, or other steering controls (not shown) that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right" steering to control a yaw of distal end 281. Steerable elongate devices are described in detail in U.S. patent application Ser. No. 13/274,208 (filed Oct. 14, 2011) (disclosing "Catheter with Removable Vision Probe"), which is incorporated by reference herein in its entirety. In embodiments in which medical instrument system 200 is actuated by a teleoperational assembly, drive unit 204 may include drive inputs that removably couple to and receive power from drive elements, such as actuators, of the teleoperational assembly. In some embodiments, medical instrument system 200 may include gripping features, manual actuators, or other components for manually controlling the motion of medical instrument system 200. Elongate device 202 may be steerable or, alternatively, the system may be non-steerable with no integrated mechanism for operator control of the bending of distal end 218. In some examples, one or more lumens, through which medical instruments can be deployed and used at a target surgical location, are defined in the walls of flexible body 216.

In some embodiments, medical instrument system 200 may include a flexible bronchial instrument, such as a bronchoscope or bronchial catheter, for use in examination, diagnosis, biopsy, or treatment of a lung. Medical instrument system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

The information from tracking system 230 may be sent to a navigation system 232 where it is combined with information from visualization system 231 and/or the preoperatively obtained models to provide the operator with real-time position information. In some examples, the real-time position information may be displayed on display system 110 of FIG. 1 for use in the control of medical instrument system 200. In some examples, control system 116 of FIG. 1 may utilize the position information as feedback for positioning medical instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 200 may be teleoperated within medical system 100 of FIG. 1. In some embodiments, teleoperational manipulator assembly 102 of FIG. 1 may be replaced by direct operator control. In some examples, the direct operator control may include various handles and operator interfaces for hand-held operation of the instrument.

Figure 3A:
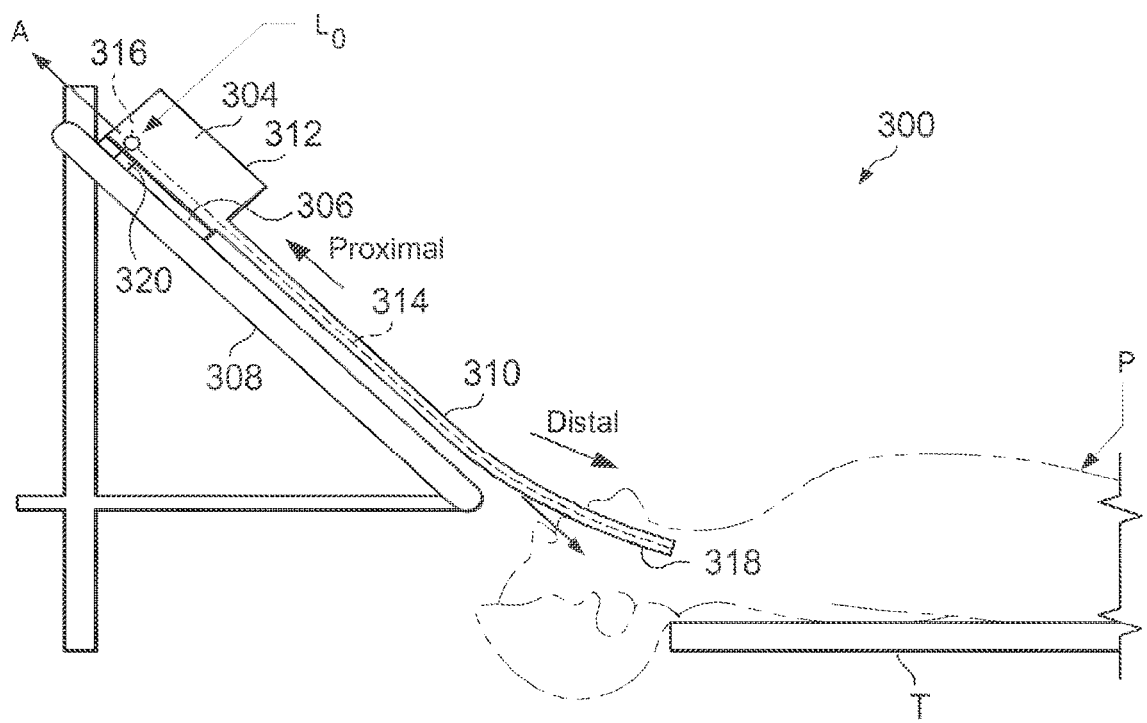
FIGS. 3A and 3B are simplified diagrams of side views of a patient coordinate space including a medical instrument mounted on an insertion assembly according to some embodiments.
Figure 3B:
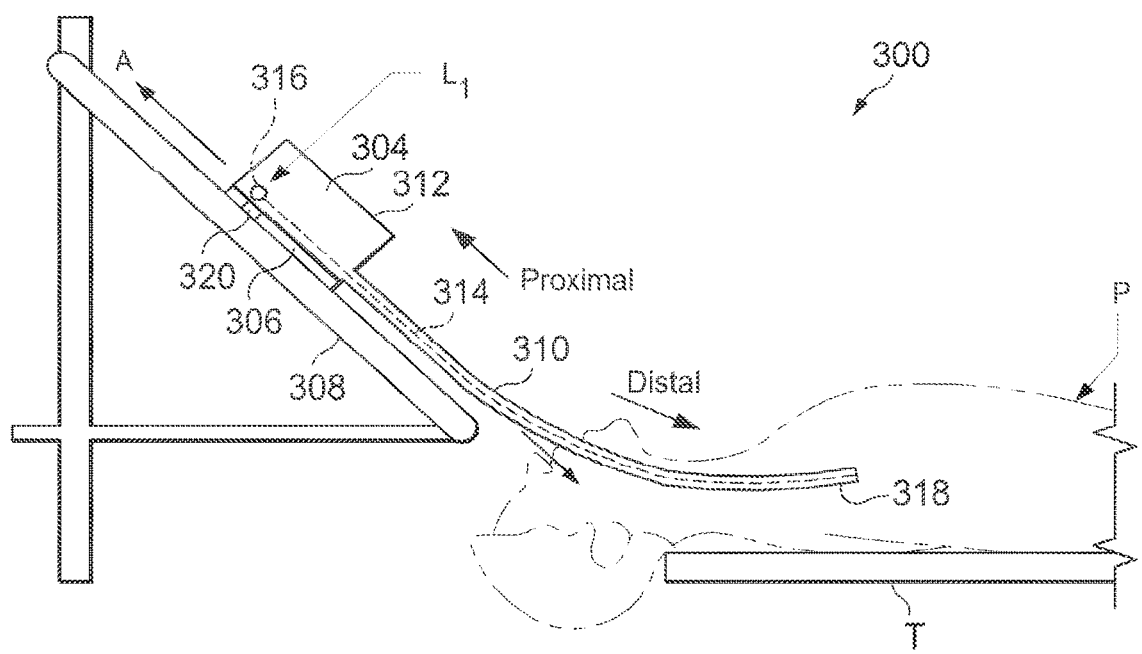

FIGS. 3A and 3B are simplified diagrams of side views of a patient coordinate space including a medical instrument mounted on an insertion assembly according to some embodiments. As shown in FIGS. 3A and 3B, a surgical environment 300 includes a patient P is positioned on platform 302. Patient P may be stationary within the surgical environment in the sense that gross patient movement is limited by sedation, restraint, and/or other means. Cyclic anatomic motion including respiration and cardiac motion of patient P may continue, unless patient is asked to hold his or her breath to temporarily suspend respiratory motion. Accordingly, in some embodiments, data may be gathered at a specific, phase in respiration, and tagged and identified with that phase. In some embodiments, the phase during which data is collected may be inferred from physiological information collected from patient P. Within surgical environment 300, a point gathering instrument 304 is coupled to an instrument carriage 306. In some embodiments, point gathering instrument 304 may use EM sensors, shape-sensors, and/or other sensor modalities. Instrument carriage 306 is mounted to an insertion stage 308 fixed within surgical environment 300. Alternatively, insertion stage 308 may be movable but have a known location (e.g., via a tracking sensor or other tracking device) within surgical environment 300. Instrument carriage 306 may be a component of a teleoperational manipulator assembly (e.g., teleoperational manipulator assembly 102) that couples to point gathering instrument 304 to control insertion motion (i.e., motion along the A axis) and, optionally, motion of a distal end 318 of an elongate device 310 in multiple directions including yaw, pitch, and roll. Instrument carriage 306 or insertion stage 308 may include actuators, such as servomotors, (not shown) that control motion of instrument carriage 306 along insertion stage 308.

Elongate device 310 is coupled to an instrument body 312. Instrument body 312 is coupled and fixed relative to instrument carriage 306. In some embodiments, an optical fiber shape sensor 314 is fixed at a proximal point 316 on instrument body 312. In some embodiments, proximal point 316 of optical fiber shape sensor 314 may be movable along with instrument body 312 but the location of proximal point 316 may be known (e.g., via a tracking sensor or other tracking device). Shape sensor 314 measures a shape from proximal point 316 to another point such as distal end 318 of elongate device 310. Point gathering instrument 304 may be substantially similar to medical instrument system 200.

A position measuring device 320 provides information about the position of instrument body 312 as it moves on insertion stage 308 along an insertion axis A. Position measuring device 320 may include resolvers, encoders, potentiometers, and/or other sensors that determine the rotation and/or orientation of the actuators controlling the motion of instrument carriage 306 and consequently the motion of instrument body 312. In some embodiments, insertion stage 308 is linear. In some embodiments, insertion stage 308 may be curved or have a combination of curved and linear sections.

FIG. 3A shows instrument body 312 and instrument carriage 306 in a retracted position along insertion stage 308. In this retracted position, proximal point 316 is at a position $L_0$ on axis A. In this position along insertion stage 308 an A component of the location of proximal point 316 may be set to a zero and/or another reference value to provide a base reference to describe the position of instrument carriage 306, and thus proximal point 316, on insertion stage 308. With this retracted position of instrument body 312 and instrument carriage 306, distal end 318 of elongate device 310 may be positioned just inside an entry orifice of patient P. Also in this position, position measuring device 320 may be set to a zero and/or the another reference value (e.g., I=0). In FIG. 3B, instrument body 312 and instrument carriage 306 have advanced along the linear track of insertion stage 308 and distal end 318 of elongate device 310 has advanced into patient P. In this advanced position, the proximal point 316 is at a position $L_1$ on the axis A. In some examples, encoder and/or other position data from one or more actuators controlling movement of instrument carriage 306 along insertion stage 308 and/or one or more position sensors associated with instrument carriage 306 and/or insertion stage 308 is used to determine the position $L_x$ of proximal point 316 relative to position $L_0$. In some examples, position $L_X$ may further be used as an indicator of the distance or insertion depth to which distal end 318 of elongate device 310 is inserted into the passageways of the anatomy of patient P.

Control of a flexible elongate device such as elongate device 202 having flexible body 216, elongate device 310, and/or a flexible catheter often involves the simultaneous control of multiple degrees of freedom. In some examples, to control insertion and/or retraction of the elongate device and correspondingly an insertion depth of the distal end of the elongate device, such as distal end 218 and/or 318, one or more actuators, such as the one or more actuators controlling the position of instrument carriage 306 along insertion stage 308, are used. Commands to the one or more actuators may be received from operator O using a single degree of freedom input control, such as a lever, joystick, and/or the like. In some examples, to control the steering of the distal end, the steering unit for the distal end, such as drive unit 204, is provided with both pitch and yaw instructions. The pitch and yaw instructions may be received from operator O using a two-degree of freedom input control, such as a joystick. Because control of the elongate device typically includes concurrently providing insertion and/or retraction instructions along with steering instructions, the input controls for insertion and/or retraction and steering are typically separate from each other.

For certain procedures, the use of levers and/or joysticks as the input controls for the elongate devices of FIGS. 2A, 3A, and/or 3B can be less than ideal. This is because levers and joysticks are input controls that have a finite length of travel, which are often disproportionately short relative to the length of insertion travel and/or the range of steering necessary to access certain anatomy. Thus, use of the levers and/or joysticks as positional input devices that provide a limited insertion depth, pitch setting, and/or yaw setting can be inadequate. Input controls with a finite length of travel are typically used as velocity input devices where either movement of the input control either specifies three velocity settings (reverse, idle, and forward) for switch-type input controls or variable velocity settings for proportional type input controls. However, velocity-based control of the insertion depth, pitch setting, and/or yaw setting is often unsatisfactory for high-precision manipulation of the elongate device as the control of the velocity of the distal end does not generally intuitively correspond with desires to make small high-precision changes in the insertion depth, pitch setting, and/or yaw setting, which is typically required for teleoperated minimally invasive medical procedures.

In contrast, input controls offering an infinite length of travel can offer better options as input controls for the elongate device when accessing certain anatomy. Input controls with an infinite length of travel correspond to input controls that allow continued movement of the inputs controls in a particular direction where no stop, such as a mechanical stop, restricts further movement. One example of a one degree of freedom input control with an infinite length of travel is a scroll wheel, which may be spun unendingly in either direction. One example of a multiple-degree of freedom input control with an infinite length of travel is a track ball, which may be spun unendingly about any number of axes, which in practice may be decomposed into combinations of a left and right rotation, a forward and back rotation, and a spin in place rotation. Other examples of input controls that support an apparent infinite length of travel are input controls that support directional swipes without movement of the input control. Examples of directional swipe input controls are touch pads, touch screens, and/or the like.

Accordingly, it would be advantageous to develop input control units for elongate devices to provide input controls having infinite length of travel along with additional input controls to support the various modes of operation for elongate device.

Figure 4:
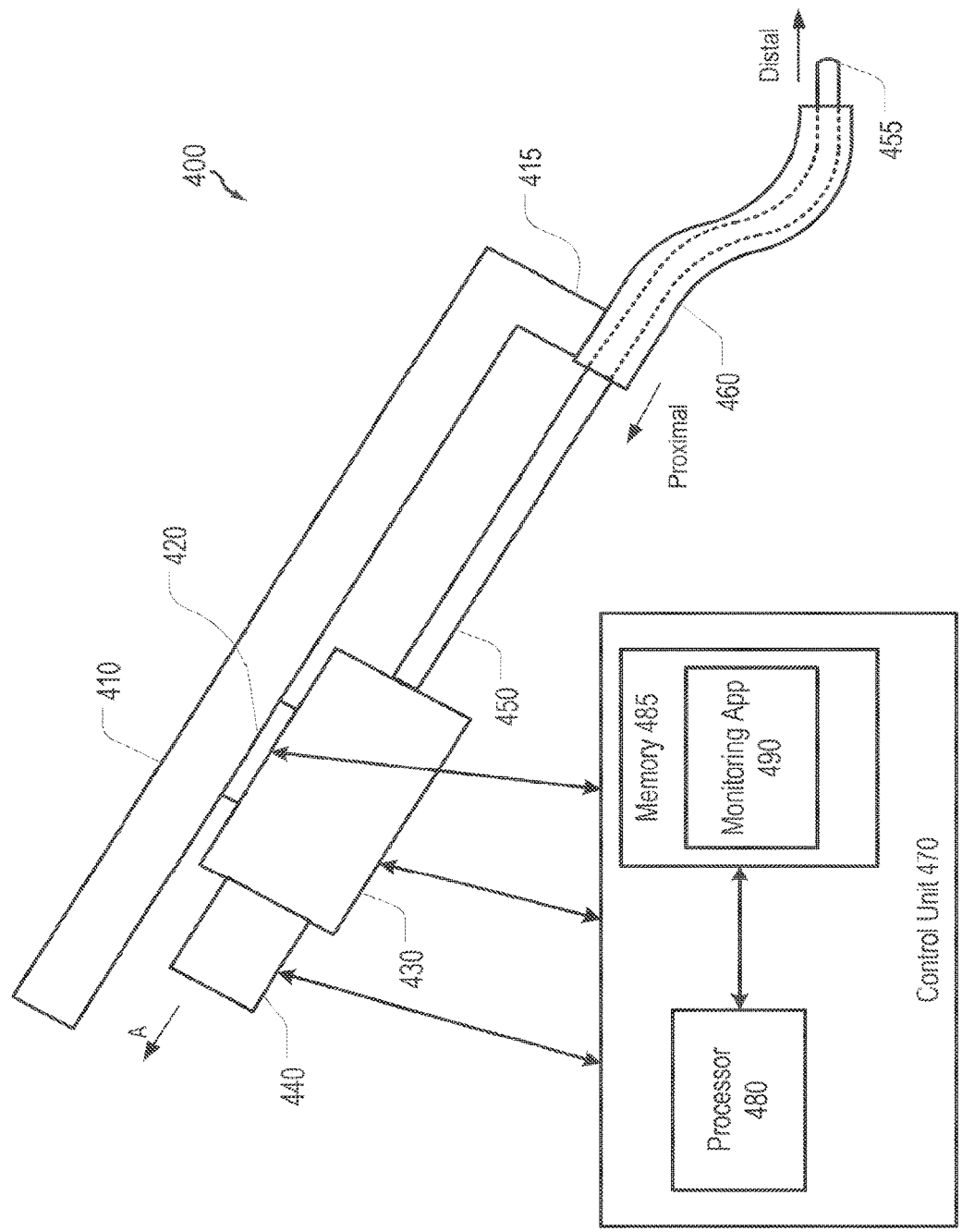
FIG. 4 is a simplified diagram of a system for monitoring an elongate device according to some embodiments.

FIG. 4 is a simplified diagram of a system 400 for monitoring an elongate device 450 according to some embodiments. FIG. 4 shows a side view of an actuation structure used to control elongate device 450 and a control system used to monitor elongate device 450 and a distal end 455 of elongate device 450 as it is being controlled. In some examples, elongate device 450 may be consistent with instrument 104, the elongate device of FIG. 2, and/or elongate device 310. System 400 includes an instrument stage 410, which may be consistent with insertion stage 308. Instrument stage 410 includes a long longitudinal span along which an instrument body 430 (which is coupled to a proximal end of elongate device 450) may be traversed. As shown, instrument body 430 is mounted via an insertion carriage 420 to instrument stage 410. As instrument body 430 is moved along instrument stage 410 (i.e., along axis A) an insertion depth of distal end 455 within one or more passageways (not shown) is controlled. Movement of insertion carriage 420 and instrument body 430 along instrument stage 410 is controlled by one or more actuators, motors, and/or the like (not shown), which may be located on instrument body 430, instrument stage 410, and/or insertion carriage 420. In some examples, insertion carriage 420 may be consistent with insertion carriage 306 and/or instrument body 430 may be consistent with instrument body 312.

Although FIG. 4 shows one possible orientation and configuration of the actuation structure for elongate device 450, it should be understood that other configurations of the various elements are possible. In some examples, instrument stage 410 may be mounted to an orientable base whose position and/or orientation (e.g., angle relative to horizontal) may be adjusted to control a position and/or orientation of the proximal end of elongate device 450. In some examples, instrument stage 410 may be mounted to an arm of an articulated device.

A tracking system 440, which may be consistent with tracking system 230, is shown attached to instrument body 430. Tracking system 440 helps track distal end 455 of elongate device 450 as it is being operated. In some examples, tracking system 440 may interface to a shape sensor, similar to shape sensor 220, for monitoring the shape of elongate device 450 and thus provide information on the position and/or orientation of distal end 455.

A distal end of instrument stage 410 includes a mounting bracket 415 that couples instrument stage 410 to a guide tube 460. In some examples, guide tube 460 may be an endotracheal tube, which may be used to guide elongate device 450 into the esophagus of a patient. Guide tube 460 includes one or more lumens through which distal end 455 and a body of elongate device 450 is passed.

Monitoring of the operation of the actuation structure and elongate device 450 is performed by a control unit 470. In some embodiments, control unit 470 may correspond to one or more portions of sensor system 108, display system 110, and/or control system 112 of FIG. 1. As shown in FIG. 4, control unit 470 includes a processor 480 coupled to memory 485. Operation of control unit 470 is controlled by processor 480. And although control unit 470 is shown with only one processor 480, it is understood that processor 480 is representative of one or more central processing units, multi-core processors, microprocessors, microcontrollers, digital signal processors, field programmable gate arrays (FPGAs), application specific integrated circuits (ASICs), and/or the like in control unit 470. Control unit 470 may optionally be implemented as a stand-alone subsystem and/or board added to a computing device or as a virtual machine. In some embodiments, control unit 470 may optionally be included as part of an operator workstation (not shown) and/or operated separately from, but in coordination with the operator workstation.

Memory 485 is used to store software executed by control unit 470 and/or one or more data structures used during operation of control unit 470. Memory 485 includes one or more types of machine-readable media. Some common forms of machine-readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

As shown, memory 485 includes a monitoring module 490 that is used to monitor the activity and movement of the actuation structure and elongate device 450. Control unit 470 is coupled to at least insertion carriage 420, instrument body 430, and/or tracking system 440 as well as to other portions of system 400 (not shown), as indicated by the representative arrows in FIG. 4, in order to provide access to signals, data, and/or other information for use by monitoring module 490. Control unit 470 may further include an input/output (I/O) interface (not shown) to help couple control unit 470 with insertion carriage 420, instrument body 430, and/or tracking system 440. The I/O interface may include one or more drivers, signal conditioners, receivers, ports, and/or the like. The I/O interface may optionally include one or more cables, connectors, ports, and/or buses, and it may optionally further include one or more networks with one or more network switching and/or routing devices. In some examples, the I/O interface may optionally include wireless interfaces.

Monitoring module 490 includes one or more sub-modules for monitoring sensors, signals, and/or other data and information related to the operation of system 400 and elongate device 450. In some examples, monitoring module 490 is responsible for determining an environmental force being exerted by elongate device 450 on the passageways through which it is being navigated (or conversely the force being exerted on elongate device 450 by the passageways), making an evaluation as to whether the environmental force is excessive for the current operating conditions, and providing feedback to the operator. The function of monitoring module 490 is particularly important when elongate device 450 is being operated teleoperatively where the operator is not able to directly sense the environmental force.

Although not shown in FIG. 4, system 400 may additionally include elements for controlling the operation of the actuation structure and elongate device 450. In some examples, memory 485 may further include one or more control applications, which share information with monitoring module 490. In some examples, system 400 may further include an operator console to allow the operator to provide teleoperative control of the actuation structure and elongate device 450. Examples of operator consoles are described in co-owned International Patent Application Serial No. PCT/US2017/039808 (filed Jun. 28, 2017) (disclosing "Systems and Methods of Steerable Elongate Device") and co-owned U.S. Provisional Patent Application Ser. No. 62/539,467 (filed Jul. 31, 2017) (disclosing "Systems and Methods of Steerable Elongate Device"), both of which are incorporated by reference herein in their entirety.

One possible approach for determining the environmental force is to equip elongate device 450 with a series of force sensors, such as strain gauges, located along the length of elongate device 450 to measure the environmental force directly. This, however, is not very practical as it could increase the complexity and the size of elongate device 450 making it less able to access narrow passageways, increase the cost, etc. Fortunately, other approaches are able to estimate the environmental force indirectly. One or more of these other approaches are used by monitoring module 490.

A first approach to estimate the environmental force indirectly is based on static and dynamic (e.g., mechanical) models of the actuation structure and elongate device 450. The forces associated with elongate device 450 may be modeled according to Equation 1.

$$(m_{Carriage} + m_{Device})\ddot{A} = F_{Gravity} + F_{Actuator} - (F_{Friction} + F_{Environment})$$ Equation 1

In Equation 1, $m_{Carriage}$ is the mass of insertion carriage 420 and instrument body 430 as well as tracking system 440, when tracking system 440 moves with instrument body 430, and $m_{Device}$ is the mass of elongate device 450. $\ddot{A}$ corresponds to the acceleration of instrument body 430, etc. in the A (insertion-retraction) direction. The masses $m_{Carriage}$ and $m_{Device}$ may be known from the models of the actuation structure and/or elongate device 450 and/or device specific values based on serial numbers of the actuation structure and/or elongate device 450, read from memory devices on the actuation structure and/or elongate device 450, inputs provided at a time of operation, and/or other approaches. The acceleration may be determined based on signals provided by one or more accelerometers on insertion carriage 420 and/or instrument body 430, determined by differentiating (e.g., using a finite difference algorithm) signals from one or more position sensors tracking the position of insertion carriage 420 relative to instrument stage 410, and/or the like.

$F_{Friction}$ is a measure of forces due to friction during movement of insertion carriage 420 along instrument stage 410 and/or relative movement between elongate device 450 and a corresponding lumen within guide tube 460. In some examples, the amount of friction may also vary based on a type and/or amount of lubrication used within the corresponding lumen. $F_{Friction}$ may be determined from one or more models of friction verified by trial motion of instrument body 430 along instrument stage 410 and elongate device 450 within the corresponding lumen of guide tube 460 along with position and velocity measurements of insertion carriage 420 and/or instrument body 430 relative to instrument stage 410. In some examples, the position and/or velocity may be determined from the one or more signals from the one or more position sensors used to determine the acceleration (using numerical differentiation to determine the velocity from the position), by integrating the acceleration (e.g., numerically via the rectangle rule, the trapezoid rule, and/or the like), and/or other similar approaches. In some examples, the one or more models of friction may be based on models of Coulombic dynamic and/or static friction, viscous friction, Stribeck friction models, Dahl friction models, LeGRE friction models, and/or the like, with the most appropriate friction model or models being selected based on empirical studies of friction in system 400. In some examples, one or more parameters for one or more of the friction models may be determined in advance for lookup during a procedure, determined during the procedure, and/or the like. In some examples, predictions from two or more friction models may be aggregated together to determine $F_{Friction}$. In some examples, different models of friction may be used for different portions of system 400 in order to determine $F_{Friction}$.

$F_{Gravity}$ is a measure of the forces due to gravity on instrument body 430 and/or elongate device 450. The direction of the gravitational forces may be determined based on the orientation of instrument stage 410 and then combined with the mass values $m_{Carriage}$ and/or $m_{Device}$.

$F_{Actuator}$ is the force being used to actuate instrument body 430 and elongate device 450 using instrument stage 410 along insertion-retraction axis A. In some examples, the actuation force may be determined from the currents and/or torques of the one or more actuators being used to drive insertion carriage 420 relative to instrument stage 410.

$F_{Environment}$ is the environmental force being asserted by elongate device 450 against the one or more passageways it is being navigated to. By factoring the known mass of the system, measuring the acceleration of insertion carriage 420, instrument body 430, tracking system 440 (if applicable), and elongate device 450, and measuring the forces of system 400 due to friction, gravity, and actuation, environmental force may be calculated by according to Equation 2.

$$F_{Environment} = -(m_{Carriage}+m_{Device})\ddot{A} - F_{Friction} + F_{Gravity} + F_{Actuator} \qquad \text{Equation 2}$$

A second approach to estimate the environmental force indirectly is based on shape measurements of elongate device 450 provided by tracking system 440. In some examples, the curvature of various portions of elongate device 450 (such as determined using the shape sensor of tracking system 440) may be used to estimate an amount of compression between the one or more segments (e.g., the one or more segments 224) used to form the body of elongate device 450. As sections of elongate device 450 are curved as they are moved through the one or more passageways, the curved sections are subject to compression (sometimes also called "prolapsing"), which elongate device 450 resists by attempting to straighten itself. This straightening force is resisted as elongate device contacts the walls of the one or more passageways. The compression force for each curved section may be determined based on one or more of a length of the section, a radius of curvature, and a mathematical model of mechanical properties of elongate device 450. In some examples, the mathematical model may be a spring model based on a spring constant and Hooke's Law. The total of the compression forces for each curved section is an estimate of the environmental force.

In some examples, the shape measurements may alternatively be used to track an expected movement distance of distal end 455 and the actual movement distance of distal end 455. Differences between the expected movement of distal end 455 (as measured at a proximal end of elongate device 450) and the actual movement of distal end 455 (as measured at a distal end of elongate device 450) are an indication of how much elongate device 450 is being compressed within the one or more passageways. The amount of compression and a spring model, similar to the spring model based on curvatures, may be used to estimate the environmental force. The expected movement of distal end 455 may be measured by tracking the position of insertion carriage 420 and/or instrument body 430 relative to instrument stage 410. The accelerometers and/or position sensors discussed above with respect to the static and dynamic models may be used to determine the expected movement of distal end 455. The actual movement of distal end 455 may be measured by tracking the actual motion of distal end 455 and computing a path length of that motion.

A third approach to estimate the environmental force indirectly is based on proximal force sensing. Proximal force sensing is not subject to the cost and/or impracticalities associated with direct force sensing as it can be accomplished using force sensors that are not positioned with the elongate, but are rather integrated into the actuation apparatus located proximal to the elongate device. These proximal force sensors typically do not increase the size of elongate device and, further, do not typically increase the cost and complexity of the elongate device, which is often a disposable component. In some examples, one or more force sensors mounted on instrument stage 410, insertion carriage 420, and/or instrument body 430 may be used to measure an amount of force being asserted to insert and/or retract elongate device 450 through the one or passageways. For example, one or more force sensors measuring a resisting force that is resisting motion of insertion carriage 420 relative to instrument stage 410 may be used to determine the proximal force, which is an estimate of the environmental force. In some examples, the one or more force sensors may include a first force sensor located at an input of a low backlash drivetrain of the actuation apparatus, a second force sensor located at an output of the drivetrain. In some examples, a difference between the forces sensed by the first and second force sensors may be applied to a compliance model for the drivetrain to determine proximal force. In some examples, the one or more force sensors may include one or more compliant and/or elastic members (e.g., as part of the kinematic structure, drivetrain, and/or the like). Each of the one or more compliant members may include a position sensor at opposite ends of each compliant member and an associated stiffness k of the compliant member, where the force exerted on each of the compliant members may be determined according to Equation 3, where $p_1$ and $p_2$ are the positions of the ends of the compliant member determined using the respective positions sensors and $d_0$ is the nominal length of the compliant member so that the force is based on the amount the compliant member is compressed or expanded relative to its nominal length. In some examples, the estimate of environmental force using this approach may be adjusted to account for friction between elongate device and the corresponding lumen of guide tube 460 as described previously. In some examples, the one or more force sensors may include one or more strain gauges, one or more spring sensors, one or more piezoelectric force sensors, and/or the like. In some examples, the one or more force sensors may be monitored so as to adjust for variations and/or deviations due to a current temperature of the one or more force sensors. In some examples, the current temperature may be determined using one or more temperature sensors located near the one or more force sensors, based on thermal indications from the FBGs in a fiber optic shape sensor, such as shape sensor 222 as described in U.S. Pat. Nos. 7,781,724, 7,772,541, and 6,389,187, and/or the like.

$$F_{Compliant\ Member} = k*((p_2-p_1)-d_0) \qquad \text{Equation 3}$$

According to some embodiments, each of the three indirect approaches may be used independently to estimate the environmental force on elongate device 450. In some examples, each of the estimates of the environmental force may be improved and become less susceptible to transient and other errors by applying a low pass filter to one or more of the sensor signals (e.g., the position provided by a position sensor, an acceleration provided by an accelerometer, a current used by one or more of the actuators, and/or the like). In some examples, one or more estimators, such as a Kalman filter, may be used to reduce transient and/or stochastic elements in the one or more signals and/or the one or more force estimates.

According to some embodiments, two or more of the three indirect approaches may be used in combination with each other to improve the estimate of the environmental force. In some examples, the estimates from the two or more approaches may be aggregated together, such as by averaging, to improve the overall estimate of the environmental force.

Monitoring module 490 further includes one or more modules for determining a force threshold used to determine whether the environmental force on elongate device 450 is excessive. In some examples, a static force threshold could be used, but that is often inadequate because a high environmental force which may be expected and/or reasonable in one circumstance may not be in others. The static force threshold, for example, is not able to distinguish between high forces due to a straight on collision between distal end 455 and a passage way wall and high forces due to friction between the sides of elongate device 450 and the walls of the one or more passageways. Accordingly, a situation specific force threshold is likely to be more useful.

In some examples, the force threshold may be determined based on a model or type of elongate device 450 (e.g., the elongate device may be a delivery catheter, ablation probe, imaging probe, biopsy needle, etc.), a type of procedure being performed using elongate device 450 (e.g., placement of a delivery catheter at a treatment site, ablation, biopsy, tumor removal, etc.), a size of the patient, a desired target location (e.g., a position within the one or more anatomical passageways, a position within an organ, a position within vasculature, etc.), operator preference, a type of tissue being navigated (e.g., the force threshold may be decreased around delicate tissues and/or near vital organs), and/or the like. In some examples, different force thresholds may be used for different operating modes and/or a driving state of elongate device 450. In some examples, a force threshold for retracting elongate device 450 may be higher or lower than a force threshold for inserting elongate device 450.

In some examples, the insertion depth of distal end 455 within the one or more passageways (e.g., as determined based on the position of insertion carriage 420 relative to instrument stage 410) may be used to determine the force threshold. In some examples, the force threshold may increase with insertion depth as there is likely to be more friction between elongate device 450 and the walls of the one or more passageways as the insertion depth increases and the elongate device enters smaller passageways and more of the elongate device 450 is inserted within the one or more passageways.

In some examples, a location of distal end 455 within the one or more passageways may be used to determine the force threshold. In some examples, the force threshold may be decreased when the distal end 455 is being inserted toward a wall of the one or more passageways. In some examples, the force threshold may be increased as insertion depth or branch depth (e.g., how many branching points, such as the main carina, within the one or more passageways are located along elongate device 450) increases. In some examples, a passageway diameter or cross-sectional area at or near distal end 455 may be used to determine the force threshold with the force threshold increasing as the passageway diameter or cross-sectional area decreases to account for the likely increase in friction between elongate device 450 and the walls of the one or more passageways. In some examples, the elongate device may be registered to one or more models of one or more passageways, for example, using one or more three-dimensional scans and/or images of the one or more passageways. In some examples, the registration may be performed by determining a current position of the elongate device with the one or more passageways (e.g., by using tracking system 230), matching that to pre-operatively obtained models of the one or more passageways (e.g., via a C-T scan). The insertion depth, the branch depth, the passageway diameter, and/or the passageway cross-sectional area at a distal end of the elongate device may be determined by using the current position within the one or more registered models. In some examples, the force threshold determined based on features of the one or more passageways may further be adjusted to account for a type, diameter, and/or length of elongate device 450.

In some examples, a measure of curvature of elongate device 450 may be used to determine the force threshold. In some examples, the measure of curvature may be obtained from a shape sensor, such as shape sensor 222. In some examples, as elongate device 450 is navigated through passageway sections having small radii of curvature, the friction between elongate device 450 and the walls of the one or more passageways is likely to increase and a higher force threshold may be appropriate. In some examples, the techniques previously discussed to determine curvature associated with the compression and/or prolapsing of elongate device 450 may additionally be used to help determine the force threshold. In some examples, the one or more models of the one or more passageways and the tracked path through the one or more passageways may be used to determine the curvature of elongate device 450. In some examples, the force threshold determined based on the curvature of the one or more passageways may further be adjusted to account for a type, stiffness, and/or length of elongate device 450.

In some examples, a type and/or an amount of lubrication used with elongate device 450 may be used to determine the force threshold. In some examples, the effects of lubrication on the force threshold may differ based on whether the lubrication is between elongate device 450 and the respective lumen within guide tube 460 and/or between elongate device 450 and the walls of the one or more passageways.

In some examples, the commanded motion of the elongate device, such as through an insertion input control, compared to the actual motion of the elongate device along an insertion axis, which can be measured using tracking system 230, position measuring device 320, and/or the like, may be used to determine the force threshold. In some examples, the type of applied threshold calculation may be based on a driving state such as insertion or retraction. For example, when the elongate device is being further inserted (e.g., advanced) into the one or more passageways, the force threshold may be determined as a change in insertion force over a change in insertion distance so that rapid increases in insertion force over a short insertion distance are detected and trigger an alert to the operator. When the elongate device is being retracted from the one or more passageways, the stiffness of the catheter may be reduced by decreasing the force or tension in the cables used to steer the distal end of the elongate device, and so the force threshold may be set at a fixed threshold or range of thresholds.

Depending upon the embodiment, the force threshold may be determined based on any of the individual factors discussed above and/or using combinations of any two or more of them. In some examples, each of the force thresholds determined using the individual factors may be aggregated together (e.g., by averaging). In some examples, a base force threshold may be used and then adjusted based on increase and/or decrease amounts contributed by other factors. For example, a base force threshold based on a desired procedure and tissue and/or passageway type may be selected with the base force threshold being adjusted during operation as the insertion depth and the curvature of elongate device 450 changes.

Monitoring module 490 further includes one or more modules for providing feedback to the operator when the estimated environmental force exceeds the force threshold. In some examples, the feedback may include one or audio and/or visual alerts to the operator that the estimated environmental force exceeds the force threshold. In some examples, the one or more alerts may include activating an alert tone, outputting a spoken message, and/or the like. In some examples, the one or more alerts may include providing physical feedback, such as vibrating one or more input controls being used by the operator to control elongate device 450.

In some examples, the feedback may include providing haptic feedback to the one or more input controls being used by the operator to control elongate device 450. In some examples, the haptic feedback may include one or more of providing force feedback to the one or more input controls, In some examples, the haptic feedback may include kinesthetic feedback where an actuator is used to adjust a resistance to the one or more input controls used to control the insertion of the elongate device and thus increase and/or decrease the amount of force the operator uses to move the insertion input control device. In some examples, the haptic feedback may include vibrotactile feedback where the actuator is used to vibrate or cause the insertion input control device to buzz. In some examples, the frequency, amplitude, and/or duration of the vibration or buzzing may be adjusted to signal different levels of haptic feedback. In some examples, the amount and/or extent of the haptic feedback may increase as the amount that the estimated environmental force exceeds the force threshold increases.

In some embodiments, motion of the elongate device may be limited or scaled depending on the estimated force. In some examples, a gain or a scale between motion of the one or more input controls and the amount of motion between insertion carriage 420 and instrument stage 410 may be changed. In another example, a current, torque, and velocity threshold may be adjusted for the one or more actuators causing the motion of insertion carriage 420 relative to instrument stage 410, and/or the like. In some examples, the haptic feedback may include blocking further insertion of distal end 455 by ignoring insert commands from the one or more input devices and preventing insertion motion of elongate device 450.

And although monitoring module 490 is depicted as a software application, monitoring module 490 may be implemented using hardware, software, and/or a combination of hardware and software.

Figure 5:
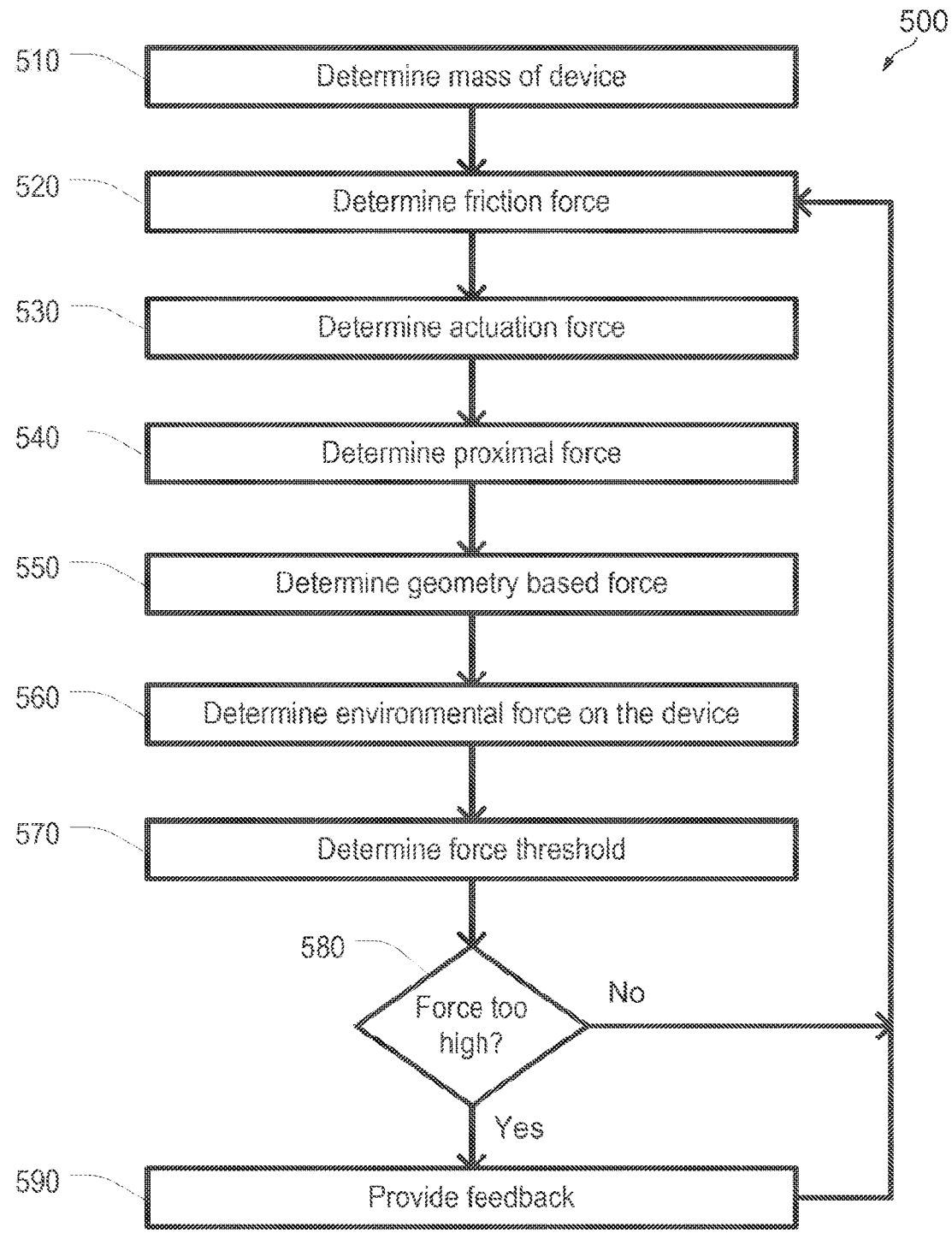
FIG. 5 is a simplified diagram of a method of operating an elongate device according to some embodiments.

FIG. 5 is a simplified diagram of a method of operating an elongate device according to some embodiments. One or more of the processes 510-590 of method 500 may be implemented, at least in part, in the form of executable code stored on non-transitory, tangible, machine-readable media that when run by one or more processors (e.g., the processor 480 in control unit 470) may cause the one or more processors to perform one or more of the processes 510-590. According to some embodiments, the order in which processes 510-590 are performed may optionally vary from the order implied by the diagram of FIG. 5. In some examples, processes 520-570 may operate in other order and/or in parallel. In some examples, processes 580 and 590 may be operated in parallel with processes 520-570 so that feedback may be constantly provided when appropriate. In some examples, one or more of processes 510-550 and/or 570 may be optional depending upon the environmental force estimation techniques used and/or how the force threshold is determined. In some examples, the loop including processes 520-590 may be operated continuously and/or at periodic intervals based on a timer. In some embodiments, method 500 may be used to monitor the operation of an elongate device, such as the elongate device of FIG. 2, elongate device 310, and/or elongate device 450.

At a process 510, a mass of the device being monitored is determined. In some embodiments, the determined mass may be the mass on an elongate device, such as elongate device 450, and/or one or more elements used to actuate the elongate device, such as insertion carriage 420, instrument body 430, and/or tracking system 440. In some examples, the mass may be the masses of Equation 1. In some examples, the mass may be determined based on models of device being monitored, device specific values based on serial numbers or read from memory devices on the device, inputs provided at a time of operation, and/or the like. In some examples, any of the techniques described previously for determining the mass may be used.

At a process 520, a friction force is determined. The friction force is determined using one or more models of friction for the device being monitored and the position and/or velocity of the device being monitored. In some examples, one or more signals from one or more accelerometers and/or position sensors may be used to determine the position and/or velocity as previously described. In some examples, a type and or amount of lubrication used with the device may further be used to determine the friction force. In some examples, any of the techniques described previously for determining the friction force may be used.

At a process 530, an actuation force for the device is determined. In some examples, the actuation force may be determined from the currents and/or torques of the one or more actuators being used to drive the device being monitored. In some examples, any of the techniques described previously for determining the actuation force may be used.

At a process 540, a proximal force is determined. In some examples, one or more proximal force sensors may be used to measure the amount of force resisting the desired motion in the device being monitored. In some examples, one or more force sensors, such as one or more strain gauges, one or more spring sensors, one or more piezoelectric force sensors, and/or the like, located between the proximal elements of the device being monitored may be used to determine the proximal force. In some examples, the one or more force sensors may include a first force sensor located at an input of a low backlash drivetrain used to actuate the device and a second force sensor located at an output of the drivetrain. In some examples, the one or more force sensors may include one or more compliant and/or elastic members, where each of the one or more compliant members may include a position sensor at each end and an associated stiffness k. In some examples, any of the techniques described previously for determining the proximal force may be used.

At a process 550, a geometry based force is determined. In some examples, the geometry based force may include forces associated with the curvature of the device, compression forces present in the device, and/or the like. In some examples, the geometry based force may be determined using differences in the amount of movement of a proximal and a distal ends of the device. In some examples, any of the techniques described previously for determining forces due to curvature, compression, and/or the like may be used.

At a process 560, an environmental force on the device is determined. In some examples, one or more of the forces determined during processes 520-550 may be used to determine the environmental force on the device. In some examples, forces due to gravity, which may be determined using any of the techniques described previously for determining the forces due to gravity, may further be used to determine the environmental force on the device. In some examples, any of the approaches for determining the environmental force described previously, either alone or in combination, may be used to determine the environmental force. In some examples, two or more estimates of the environmental force on the device may be aggregated together to determine the environmental force. In some examples, one or more estimators, such as a Kalman filter, may be used to reduce transient and/or stochastic elements in the determination of the environmental force on the device.

At a process 570, a force threshold is determined. In some examples, the force threshold may be static throughout a procedure and/or dynamic as the device is operated. In some examples, the force threshold may be determined based on a type or model of the device, a type of procedure being performed using the device, a type of motion being performed, a size of the patient, a desired target location for the procedure, operator preference, a type of tissue around the device, and/or the like. In some examples, different force thresholds may be used for different operating modes of the device, such as using a force threshold for retracting that may be higher or lower than a force threshold for inserting. In some examples, the force threshold may be determined and/or adjusted based on an insertion depth of the device, a branch depth of the device, a size of passageways through which a distal end of the device is being navigated, a curvature of the device, an type and/or amount of lubrication used with the device, and/or the like. In some examples, any of the techniques described previously for determining the force threshold may be used.

At a process 580 it is determined whether the environmental force determined during process 560 is higher than the force threshold determined during process 570. When the environmental force is not higher than the force threshold, the force and threshold determinations are repeated by returning to process 520. When the environmental force is higher than the force threshold, feedback is provided using a process 590.

At the process 590, feedback is provided to the operator of the device. In some examples, feedback may be provided to the operator using an audio and/or visual alert using any of the alerts described previously. In some examples, the feedback may include haptic feedback to the operator using any of the haptic feedback approaches described previously. In some examples, the amount of feedback provided may be increased as the amount that the environmental force determined during process 560 is higher than the force threshold increases. In some examples, input motion is scaled based on a magnitude of determined environmental force. Once the feedback is provided, the force and threshold determinations are repeated by returning to process 520.

As discussed above and further emphasized here, FIG. 5 is merely an example which should not unduly limit the scope of the claims. One of ordinary skill in the art would recognize many variations, alternatives, and modifications. According to some embodiments, method 500 may be modified to provide feedback according to a series of hazard levels. In some examples, process 570 may be modified to determine a series of two or more force thresholds representing different levels of hazard due to the environmental force determined during process 560. In some examples, processes 580 and 590 may be modified to provide feedback in the form of an alert level depending on which of the force thresholds the environmental force is above and which force thresholds the environmental force is below. In some examples, the danger and/or urgency of the alert level may be indicated by a color between green (no alert) through yellow to red (highest alert level), an amount of haptic feedback, a rate of beeping, and/or the like.

One or more elements in embodiments of the invention (e.g., the processing of signals received from the input controls and/or control of the elongate device) may be implemented in software to execute on a processor, such as process 480 and/or a processor of control system 112. When implemented in software, the elements of the embodiments of the invention are essentially the code segments to perform the necessary tasks. The program or code segments can be stored in a non-transitory machine-readable storage media, including any media that can store information including an optical medium, semiconductor medium, and magnetic medium. Machine-readable storage media examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc. As described herein, operations of accessing, detecting, initiating, registered, displaying, receiving, generating, determining, moving data points, segmenting, matching, etc. may be performed at least in part by the control system 112 or the processors thereof.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A medical system comprising:
a flexible elongate instrument; and
a control unit configured to:
determine a force exerted by the flexible elongate instrument on tissue of a patient;
determine a driving state of the flexible elongate instrument;
set a force threshold based on the driving state, wherein different driving states are associated with different force thresholds; and
provide feedback to an operator in response to the determined force being higher than the force threshold.

2. The medical system of claim 1, further comprising an actuator for inserting and retracting the flexible elongate instrument.

3. The medical system of claim 2, wherein the control unit determines the force based on one or more of:
a shape of the flexible elongate instrument;
a force being exerted by the actuator; or
an amount of force being applied at a proximal end of the flexible elongate instrument.

4. The medical system of claim 3, wherein the control unit determines the shape of the flexible elongate instrument using a shape sensor.

5. The medical system of claim 3, wherein to determine the force exerted by the actuator the control unit determines a current used to drive the actuator.

6. The medical system of claim 1, wherein the control unit is further configured to:
determine a plurality of force thresholds for the medical system; and
provide an alert to the operator, the alert depending on which of the plurality of force thresholds the force exerted by the flexible elongate instrument on the tissue of the patient is higher than and which of the plurality of force thresholds the force exerted by the flexible elongate instrument on the tissue of the patient is lower than, the alert indicating an alert level regarding the force exerted by the flexible elongate instrument on the tissue of the patient.

7. The medical system of claim 1, wherein the driving state includes insertion.

8. The medical system of claim 7, wherein when the driving state includes insertion, the control unit further provides the feedback to the operator when a change in force over a change in insertion distance is higher than a threshold.

9. The medical system of claim 1, wherein the driving state includes retraction.

10. The medical system of claim 9, wherein when the driving state includes retraction, the force threshold is a fixed threshold.

11. A method of operating a medical system, the method comprising:
determining a force exerted by a flexible elongate instrument on tissue of a patient;
determining a driving state of the flexible elongate instrument;
setting a force threshold based on the driving state, wherein different driving states are associated with different force thresholds; and
providing feedback to an operator in response to the determined force being higher than the force threshold.

12. The method of claim 11, further comprising determining a shape of the flexible elongate instrument using a shape sensor.

13. The method of claim 11, further comprising determining a force exerted on the flexible elongate instrument by an actuator by determining a current used to drive the actuator.

14. The method of claim 11, wherein determining the force exerted by the flexible elongate instrument on the tissue of the patient comprises:
determining one or more of:
a mass of the flexible elongate instrument;
an acceleration of a proximal end of the flexible elongate instrument;
an amount of friction in the medical system; or
an effect of gravity on the medical system and the flexible elongate instrument; and
applying a mechanical model of the medical system.

15. The method of claim 14, wherein determining the amount of friction comprises using a friction model of the medical system.

16. The method of claim 11, further comprising determining an amount of force being applied to a proximal end of the flexible elongate instrument using a force sensor located proximal to the proximal end of the flexible elongate instrument.

17. The method of claim 11, wherein setting the force threshold is further based on one or more of a model of the medical system, a model of the flexible elongate instrument, a size of passageways through which the flexible elongate instrument is being navigated, a desired target location for a distal end of the flexible elongate instrument, a type of tissue through which the flexible elongate instrument is being navigated, a type of procedure being performed, or an operator preference.

18. The method of claim 11, further comprising determining the force threshold based on one or more of an insertion depth of the flexible elongate instrument within one or more passageways, a branch depth of the flexible elongate instrument within the one or more passageways, a diameter or cross-sectional area of the one or more passageways near a distal end of the flexible elongate instrument, whether the distal end is being inserted toward a wall of the one or more passageways, or a curvature of the flexible elongate instrument.

19. The method of claim 11, further comprising:
determining a plurality of force thresholds for the medical system; and
providing an alert to the operator, the alert depending on which of the plurality of force thresholds the force exerted by the flexible elongate instrument on the tissue of the patient is higher than and which of the plurality of force thresholds the force exerted by the flexible elongate instrument on the tissue of the patient is lower than, the alert indicating an alert level regarding the force exerted by the flexible elongate instrument on the tissue of the patient.

20. A non-transitory machine-readable medium comprising a plurality of machine-readable instructions which when executed by one or more processors associated with a device are adapted to cause the one or more processors to perform a method comprising:
determining a first force exerted by a flexible elongate instrument on tissue of a patient;
determining a driving state of the flexible elongate instrument;
setting a force threshold based on the driving state, wherein different driving states are associated with different force thresholds; and
providing feedback to an operator in response to the determined first force being higher than the force threshold.

* * * * *